United States Patent [19]

Katsura et al.

[11] Patent Number: 4,792,433
[45] Date of Patent: Dec. 20, 1988

[54] CO GAS DETECTING DEVICE AND CIRCUIT FOR DRIVING THE SAME

[75] Inventors: Masaki Katsura, Yokosuka; Masayuki Shiratori, Kawasaki, both of Japan

[73] Assignee: Tokyo Shibaura Denki Kabushiki Kaisha, Kawasaki, Japan

[21] Appl. No.: 903,839

[22] Filed: Sep. 4, 1986

Related U.S. Application Data

[63] Continuation of Ser. No. 525,485, Aug. 22, 1983.

[30] Foreign Application Priority Data

Aug. 27, 1982 [JP] Japan .................. 57-147788
Nov. 30, 1982 [JP] Japan .................. 57-208480

[51] Int. Cl.$^4$ ........................................ G01N 27/16
[52] U.S. Cl. ........................................ 422/98; 73/23; 324/715; 338/225 D; 422/90
[58] Field of Search ........... 73/23, 27 R; 324/71.5; 338/34, 225 D; 422/94–98, 90; 436/134, 151, 152, 159

[56] References Cited

U.S. PATENT DOCUMENTS

| | | | |
|---|---|---|---|
| 3,961,248 | 6/1976 | Kawamura | 422/98 |
| 4,000,089 | 12/1976 | Senda | 73/27 R |
| 4,033,169 | 7/1977 | Fujishiro et al. | 422/96 |
| 4,107,019 | 8/1978 | Takao et al. | 204/425 |
| 4,193,964 | 3/1980 | John | 436/152 |
| 4,223,550 | 9/1980 | Takahama et al. | 422/98 |
| 4,251,225 | 2/1981 | Handa et al. | 422/98 X |
| 4,259,292 | 3/1981 | Ichinose et al. | 324/71.5 |
| 4,343,768 | 8/1982 | Kimura | 422/98 X |
| 4,481,499 | 11/1984 | Arima et al. | 422/98 X |

FOREIGN PATENT DOCUMENTS

| | | | |
|---|---|---|---|
| 46989 | 3/1982 | European Pat. Off. | 422/98 |
| 2636178 | 3/1977 | Fed. Rep. of Germany | 324/71.5 |
| 2746381 | 4/1978 | Fed. Rep. of Germany | |
| 3005528 | 8/1980 | Fed. Rep. of Germany | |
| 54-134697 | 10/1979 | Japan | 422/98 |
| 2086583 | 9/1981 | United Kingdom | |

*Primary Examiner*—Michael S. Marcus
*Attorney, Agent, or Firm*—Foley & Lardner, Schwartz, Jeffery, Schwaab, Mack, Blumenthal & Evans

[57] ABSTRACT

Disclosed is a CO gas detecting device which comprises a CO gas sensor provided with a gas sensitive member made of $SnO_2$, $ZnO$, $Fe_2O_3$ or the like, a pair of electrodes provided on said gas sensitive member, and a catalyst layer comprising at least one kind of catalyst metals of Pt, Pd and Rh and at least one kind of carriers of $Al_2O_3$, $ZrO_2$ and $SiO_2$, provided on said gas sensitive member; and a reference sensor substantially without sensitivity to CO gas provided with a gas sensitive member similar to the above gas sensitive member, a pair of electrodes provided on said gas sensitive member and a catalyst layer comprising Ag and at least one kind of carriers of $Al_2O_3$, $ZrO_2$ and $SiO_2$, provided on said gas sensitive member. Also disclosed is a circuit for driving the device.

16 Claims, 6 Drawing Sheets

CO GAS DETECTING DEVICE AND CIRCUIT FOR DRIVING THE SAME

This application is a continuation of application Ser. No. 525,485, filed Aug. 22, 1983.

This invention relates to a CO gas detecting device and a circuit for driving the same.

It has heretofore been known to employ a gas sensitive element using an oxide semiconductor exhibiting N-type semiconductor characteristics such as $SnO_2$, ZnO, $Fe_2O_3$, etc. for detection of a reducing gas in the air. This utilizes the phenomenon that, when these metal oxide semiconductors are contacted with a reducing gas, their electroconductivities are increased, namely to result in decrease of resistance values.

The gas sensitive element employed may be either of a sintered product type or a thin film type provided by the sputtering method or the vapor deposition method. However, any one of the sintered product type and the thin film type is generally small in its sensitivity with a metal oxide semiconductor alone and is not also sufficient is selectivity. Therefore, it is usually attempted to enhance the sensitivity of an element by use of a noble metal such as platinum (Pt), palladium (Pd), etc. as the catalyst. That is, there is generally employed a method to add Pt, Pd directly to a metal oxide semiconductor or to form a catalyst layer carrying Pt, Pd on a metal oxide semiconductor.

When such a treatment is applied, sensitivity can be improved as compared with the case in absence of the catalyst, but the resultant element cannot yet exhibit sufficient sensitivity to a reducing gas at a low concentration. Besides, when various reducing gases are present as a mixture, it is very difficult to detect only a certain gas selectively, because erroneous actuations of the element are induced by the influence of other reducing gases. Above all, concerning a gas having deleterious effects on human bodies even at a low concentration such as CO, it has been very difficult to detect such a gas while precluding the erroneous actuations caused by other reducing gases.

Further, on the supposition that a gas sensitive element is to be used in homes in general, it will become a critical problem to preclude the erroneous actuation by alcoholic vapor.

This invention has been accomplished with considerations about the points as mentioned above, and an object thereof is to provide a gas detecting device which can detect selectively CO gas.

This invention is a gas detecting device provided with a CO gas sensor (i.e., a gas sensitive element for detection of CO gas) and a reference sensor (i.e., a gas sensitive element for reference), which performs gas detection through judgement of an output from the CO gas sensor with reference to the output from the reference sensor.

According to this invention, there is provided a CO gas detecting device, comprising:

a CO gas sensor provided with a gas sensitive member comprising an oxide semiconductor of which resistance value is changed when contacted with a reducing gas, a pair of electrodes provided on said gas sensitive member, and a catalyst layer comprising at least one kind of catalyst metals of Pt, Pd and Rh and at least one kind of carriers of $Al_2O_3$, $ZrO_2$ and $SiO_2$, provided on said gas sensitive member; and a reference sensor substantially without sensitivity to CO gas provided with a gas sensitive member comprising an oxide semiconductor of which resistance value is changed when contacted with a reducing gas, a pair of electrodes provided on said gas sensitive member, and a catalyst layer comprising Ag and at least one kind of carriers of $Al_2O_3$, $ZrO_2$ and $SiO_2$, provided on said gas sensitive member.

This invention will be described below in detail with reference to the accompanying drawings.

The CO gas sensor to be used in the present invention has a gas sensitive member comprising an oxide semiconductor sensitive to a reducing gas containing CO gas, with its resitance value being changed on contact with a reducing gas, a pair of electrodes provided on said gas sensitive member and a catalyst layer comprising at least one kind of the catalyst metals of Pt, Pd and Rh and at least one kind of carriers of $Al_2O_3$, $ZrO_2$ and $SiO_2$, provided on said gas sensitive member.

As the oxide semiconductor to be used for the gas sensitive member, there may be employed $SnO_2$ type, ZnO type and $Fe_2O_3$ type semiconductors. The $SnO_2$ type, ZnO type and $Fe_2O_3$ type semiconductors comprise $SnO_2$, ZnO and $Fe_2O_3$ as the main component, respectively, and may optionally incorporate auxiliary components such as $Nb^{5+}$, $Sb^{3+}$, $Cr^{3+}$, $Al^{3+}$, etc. This gas sensitive member may be either of a thick film (herein meant by a film obtained by a so-called thick film method, i.e. a sintered product) or of a thin film (herein meant by a film obtained by a so-called thin film method), but preferably of a thin film for good response to gas as well as good reproducibility in manufacturing.

As the method for preparation of the thin film for gas sensitive member, there may be included vapor deposition, sputtering and pyrolysis of an organic compound of a metal. The gas sensitive member is formed on a ceramic substrate of $Al_2O_3$, BN, $Si_3N_4$, $SiO_2$, etc. which is a heat-resistant and insulating substrate, and its film thickness should preferably be 100 Å to 1 μm, more preferably 1000 Å to 1 μm. This is because, sensitivity to a reducing gas is lowered with a film thickness exceeding 1 μm, while a film thickness of less than 1000 Å, particularly less than 100 Å will result in lowering of sensitivity simultaneously with scattering of the sensitivity values.

In a most preferred embodiment of this invention, the gas sensitive member is a $SnO_2$ thin film or a $SnO_2$ thin film containing Nb, Sb which is prepared by pyrolysis of an organic compound containing Sn or a mixture of an organic compound containing Nb or Sb and an organic compound containing Sn. This thin film may be prepared in the following manner.

First, an organic compound containing Sn such as a metal salt of tin (e.g. tin 2-ethylhexanoate) or a resin salt containing Sn, an alkoxide of tin (ROSn, where R is an alkyl group), further an organometallic compound of tin (RSn, where R is an alkyl group or an aryl group), etc. or a mixture of such a compound mixed with a predetermined amount of an organic compound containing Nb or Sb is dissolved in a suitable solvent such as toluene, benzene, n-butyl alcohol, etc. to prepare a sample solution of a desired Sn concentration. The Sn concentration may be preferably within the range of from 1.0 to 20 wt.%.

Next, the sample solution is coated on the surface of a insulating substrate having a pair of electrodes, left to stand in the air for a predetermined period of time (usually 30 minutes to 1 hour) and then heated at an appropriate temperature (usually about 120° C.) to vaporize the solvent. Then, the whole assembly is baked in the air at a temperature of 400° to 700° C. for 30 minutes to 1 hour, whereby the organic compound containing Sn is pyrolyzed and at the same time Sn is oxidized to form a $SnO_2$ thin film. By repeating the coating-baking step several times, which cannot be determined equally but varies depending on the Sn concentration in the sample solution employed, say about 1 to 4 times, a $SnO_2$ thin film with a desired film thickness is formed.

When a thin film 3 having incorporated Nb or Sb is prepared, either one of Nb and Sb functions as donor. Nb or Sb may preferably be added to a content within the range from 0.005 to 0.05 in terms of the atomic ratio to Sn (Nb/Sn or Sb/Sn).

The gas sensitive member as obtained in the above is provided with a pair of electrodes for detection of resistance values, and the electrodes are only required to be electrically connected to the gas sensitive member, either on the surface or on the side of the substrate surface. Said electrodes may be formed of Au, Pt, etc. according to the printing method, the vapor deposition method, the sputtering method, etc. Lead wires are also generally connected for taking out electrical signals from the gas sensitive element, and for this purpose, the lead wire connecting portion may be formed by the printing method with greater bonding strength to the substrate, while the contacted portion with the gas sensitive member may be a thin film formed by the vapor deposition method, etc.

As the catalyst layer, there may be employed one comprising at least one kind of metal catalysts of Pt, Pd and Rh and at least one kind of carriers of $Al_2O_3$, $ZrO_2$ and $SiO_2$, which should preferably be porous to the extent so as not to prevent the gas sensitive member from contact with the atmospheric gas to be measured. So far as such a porosity can be satisfied, there may be employed either the thick film of a sintered product or the thin film prepared according to sputtering, vapor deposition or pyrolysis of an organometallic compound. This catalyst metal is employed for improvement of gas sensitive characteristics such as gas response, gas selectivity, etc. and the carrier is employed for the purpose of prevention of lowering of the gas sensitivity characteristics which may be caused by agglomeration of the catalyst metal during usage of the gas sensitive element. In case of a thick film, its thickness may preferably be 10 to 50 μm, and the catalytic effects such as sensitivity, selectivity, etc. will be lowered outside of said range. In case of a thin film, its thickness may preferably be about 5 to 1000 nm, particularly preferably 50 to 1000 nm in case of the pyrolysis method. Outside of said range, in addition to lowering of the catalytic effects such as sensitivity, selectivity etc., the gas response speed is also lowered.

The catalyst metal in the catalyst layer may be contained, based on $Al_2O_3$, $ZrO_2$ and or $SiO_2$, in an amount preferably of 0.05 to 20 wt.% in case of a thick film, or preferably of 1 to 90 wt.% in case of a thin film, particularly preferably 1 to 80 wt.% in case of the sputtering method. The proportion of the catalyst metals may preferably be Pt/Pd=0.05 to 1.0 in terms of the atomic ratio in case of Pt-Pd, Rh/Pd=0.05 to 1.0 in case of Pd to Rh and Rh/Pt=0.05 to 1.0 in case of Pt-Rh. Outside of the above ranges, no sufficient sensitivity and selectivity can be obtained, and further increase of the content of the metal catalyst may impart electroconductivity so much to the catalyst layer as to hamper measurement of the resistance value of the gas sensitive member. Such a catalyst layer may be either a thick film or a thin film, but preferably a thin film formed without the sintering step such as by sputtering, vapor deposition, pyrolysis of an organometallic compound or CVD (chemical vapor deposition), from the standpoint of the life of the gas sensor and gas response characteristic. For the purpose of maintaining insulation between the catalyst layer and the gas sensitive member as well as prevention of diffusion of the catalyst metal, the catalyst layer may be provided through an intermediary layer such as of $Al_2O_3$, etc.

In another embodiment of this invention, the above catalyst layer may be a layer further containing 0.05 to 20 wt.% of Ag, based on $Al_2O_3$, or the one whose surface is additionally coated with another layer comprising at least one kind of carriers of $Al_2O_3$, $ZrO_2$ and $SiO_2$ and 0.05 to 20 wt.% of Ag supported on the carrier(s). This embodiment enables to improve moisture resistance of the gas detecting device of this invention.

The CO gas sensor having a constitution as described above has sensitivities to CO and other reducing gases (herein often referred to as miscellaneous gases). It is generally also provided with a heater for heating the gas sensitive member for the purpose of improvement of gas response characteristic, etc. to carry out measurement by heating the gas sensitive member. With such a CO gas sensor, the sensitivity to CO gas can be particularly improved by making the element temperature to a low temperature of 120° C. or lower.

In the following, descriptions are made as to the reference sensor.

The reference sensor has sensitivities to gases other than CO gas. Its constitution is the same as the CO gas sensor, the gas sensitive member being the same, except for difference in the catalyst layers employed.

The catalyst layer in the reference sensor comprises Ag and at least one carriers of $Al_2O_3$, $ZrO_2$ and $SiO_2$, and may preferably be porous to the extent such that it may not prevent the gas sensitive member from contact with the atmospheric gas to be measured.

The catalyst layer may be either a thin film or a thick film similarly as in the case of the CO gas sensor, but preferably a thin film formed without the sintering step by sputtering, vapor deposition, pyrolysis of an organometallic compound, etc. The content of Ag in the catalyst layer supported on $Al_2O_3$, etc., may be preferably about 0.05 to 20 wt.% in the case of a thick film and about 1 to 80 wt.% in the case of a thin film. Outside of said range, none of sensitivity, selectivity and humidity resistance obtained are excellent, and further increase of the Ag content will make the catalyst layer electroconductive. The catalyst layer may have a thickness preferably of about 10 to 50 μm in the case of a thick film, or preferably of a thickness of about 5 to 1000 nm in the case of a thin film. Outside of said range, in addition to lowering in the catalytic effects, the gas response speed is also retarded by increase of the film thickness.

The reference sensor having such a constitution as described above has no substantial sensitivity to CO gas but has sensitivities to reducing gases (miscellaneous gases) such as alcohol gases, $CH_4$, $C_3H_8$, etc.

In the present invention, since it is possible to obtain separately the output having the information of CO gas and miscellaneous gases from the CO gas sensor and the reference output having only the information of miscellaneous gases from the reference sensor, the influence by the miscellaneous gases can easily be removed from the output of the CO gas sensor by the reference output of the reference sensor, whereby selectivity of measurement of CO gas can be improved.

Figure 1:
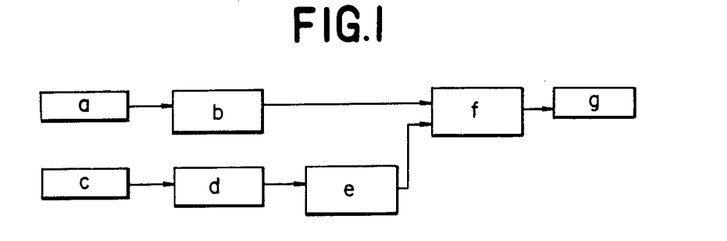
FIG. 1 is a block diagram showing an example of a circuit for driving the CO gas detecting device of this invention.

Referring now to the block diagram in FIG. 1, description is made about an example of the circuit constitution for driving the CO gas detecting device by use of such two gas sensors.

Outputs $R_1$ and $R_2$ from the CO gas sensor (a) and the reference sensor (c) for reference, respectively, are inputted in resistance-voltage converting circuits (b) and (d) to be converted to voltages $V_1$ and $V_2$, respectively. The $V_2$, which is a signal originated from the reference sensor (C) and outputted from the resistance-voltage converting circuit (d), is inputted in a circuit (e) for setting alarm level to output the alarm level $V_2'$. This $V_2'$ and the $V_1$, which latter is the signal from the CO gas sensor, are inputted in the voltage comparison circuit (f) and, when CO gas is judged to be present by this voltage comparison circuit (f), an alarm signal S is outputted therefrom and inputted to the alarm circuit (g).

In the following, actuation of this circuit is to be explained.

The resistance values $R_1$ and $R_2$, which are outputs from the CO gas sensor (a) and the reference sensor (c) are changed depending on the atmosphere to be measured. In general, the change in a gas sensitive element is abrupt at lower gas concentrations, but the slope of change becomes gentle as the gas concentration is higher. This tendency is the same with a gas mixture of two kinds or more. When CO gas is introduced in reducing miscellaneous gases, the resistance change of the gas sensitive element is smaller as compared with the case when the same amount of CO gas is introduced into the air. That is, the resistance change of the element to a constant volume of CO gas becomes smaller as the increase in the concentration of reducing miscellaneous gases in the atmosphere. Therefore, it is necessary to change the alarm level in correspondence to the concentration of the miscellaneous gases in the atmosphere to be measured. Setting of this alarm level is done by the alarm level setting circuit (e). In the alarm level setting circuit (e), $V_2$ ($R_2$) which is the signal from the reference sensor is utilized to output the alarm level $V_2'$ of CO gas of the CO gas sensor (a) in the atmosphere containing miscellaneous gases. By comparison between the alarm level $V_2'$ which is changed depending on the concentration of miscellaneous gases and $V_1$ which is the signal from the CO gas sensor (a), judgement of the presence of CO gas can be performed.

Figure 2:
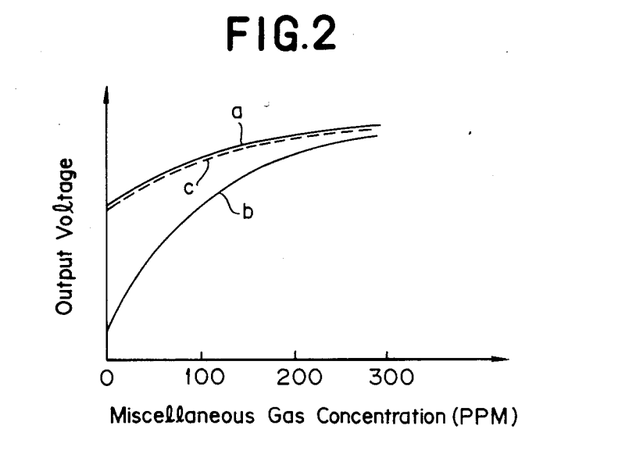
FIG. 2 is a diagram showing characteristics curves of the sensitivities to miscellaneous gas concentration, of both of the gas sensitive elements used in this invention.

FIG. 2 shows the changes of sensitivities of both the gas sensors according to this invention, depending on the concentration of miscellaneous gases. The CO gas sensor and the reference sensor are actuated in response to miscellaneous gases alone to show changes in resistance, indicating the characteristics of the output from resistance-voltage circuit as shown by the curve a in FIG. 2. When a certain volume of CO gas is introduced, the CO gas sensor will exhibit the characteristic as shown by the curve b. Accordingly, the differential voltage between the curve a and the curve b is the signal by CO gas, which differential volage between the curve a and the curve b differs greatly even at a constant level of CO gas quantity depending on the concentration of miscellaneous gases, as can be seen from the same Figure. Therefore, by changing as shown in the curve c an alarm level which is an output from the alarm level-setting circuit, based on the output of the reference sensor, the erroneous actuations due to the change in the concentration of miscellaneous gases can be cancelled.

As the resistance-voltage converting circuit, there may be employed, for example, a circuit in which a gas sensitive element and a fixed resistor are connected in series so as to measure the voltage between the both terminals of the fixed resistor by application of a constant voltage.

The alarm level-setting circuit may be constituted by, for example, combining a conventional operational amplifier with a reference voltage generating circuit, whereby the output $V_2$ (miscellaneous gas concentration-voltage) from the reference sensor is converted according to a previously set function to an output $V_1$ of the CO gas sensor in a gas mixture of miscellaneous gases and CO gas.

As the voltage comparison circuit, there may be employed a conventional electronic circuit, and as the alarm circuit, there may be employed one capable of generating or displaying alarm by buzzer, LED (light emitting diode), etc., which may also be constituted to shut down gas supply, if desired.

By use of the circuits with the constitutions as described above, the alarm level can be varied depending on the miscellaneous gas concentration, whereby CO gas can be detected with good selectivity and high reliability.

As described above, by use of a CO gas detecting device provided with a CO gas sensor having sensitivities to reducing gases containing CO gas and a reference sensor having substantially no sensitivity to CO gas according to the present invention, CO gas can be detected with good selectivity.

This invention will be described in greater detail by the following Examples.

EXAMPLE 1

Figure 3:
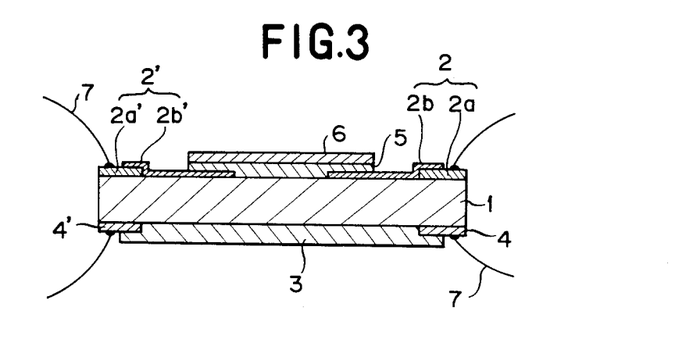
FIG. 3 is a sectional view of a gas sensitive element used in this invention.

Preparation of a CO gas sensor is to be described first. FIG. 3 shows a sectional view of a gas sensitive element. As insulating substrate 1, an alumina substrate is employed and electrodes 2, 2' are formed on one surface thereof. The electrodes 2, 2' respectively have lead wire-connecting portions 2a, 2a' and signal taking-out portions 2b, 2b' and the lead wire connecting portions 2a, 2a' are formed by baking of Au paste, while the signal taking-out portions 2b, 2b' contacted with gas sensitive member 5 is subjected to sputtering with Au to form a pair of comb-shaped electrodes. On the backside of the insulating substrate 1, there is also provided a heater 3, comprising $RuO_2$ paste, etc., for heating of the gas sensitive member 5 between the pair of electrodes 4, 4'. Lead wires are designated by numeral 7.

Then, the gas sensitive member 5 is to be formed: A sample solution was prepared by dissolving tin 2-ethylhexanoate in n-butanol to a Sn content of 10 wt.%. This was coated between the pair of electrodes 2, 2', left to stand in the air for one hour and then heated to 120° C. to vaporize n-butanol. Then, the whole composite was pyrolyzed by heating at 400° C. in the air for one hour. This coating-pyrolysis step was repeated three times to form a plate-like gas sensitive member 5 comprising a $SnO_2$ thin film with a thickness of about 0.3 μm.

As the next step, a catalyst layer 6 is to be formed on the gas sensitive member 5: To an alkoxide of Al were added resin salts of Pd and Pt (e.g. Platinum resinate, Palladium resinate, produced by ESL Co.), and the mixture was diluted with butanol. The butanol solution was coated on the gas sensitive member 5, dried at room temperature for 1 hour, then at 150° C., followed by pyrolysis by heating at 400° C. for 30 minutes, to form a catalyst layer 6 comprising $Pd-Pt-Al_2O_3$ and having thickness of 0.5 μm.

Similarly, also prepared were those having the catalyst layers comprising $Pt-Rh-Al_2O_3$, $Pd-Al_2O_3$, $Rh-Al_2O_3$, $Pd-Rh-Al_2O_3$, $Pt-Rh-Al_2O_3$ and $Pd-Pt-Rh-Al_2O_3$, respectively.

As the organic compound of the metal to be used for formation of such gas sensitive members and catalyst layers, there may be employed metal alcoholates, metal soaps, resin salts, complexes or other compounds of Pt, Pd, Rh, Al, Zr, Si capable of forming metals or metal oxides through decomposition by heating.

Such an organic compound of a metal may be dissolved in an organic solvent such as lavender oil, petroleum ether, hexane, toluene, etc. and coated on the surface of a gas sensitive member to form a film. The composition ratio of the catalyst layer can be controlled easily by changing the amounts of the organic compounds of metals in the solution. After film formation, drying treatment may preferably be applied at room temperature for about one hour and at 100° to 150° C. for about one hour to evaporate the organic solvent, thereby fixing the organic compounds of metals on the gas sensitive member.

The organic compounds of metals can be heated to be readily pyrolyzed into metals or metal oxides. And, at least one kind of Al, Zr and Si is oxidized, through the reaction with oxygen atoms in organic compounds or by heating in an atmosphere in the presence of oxygen, to be converted to $Al_2O_3$, $ZrO_2$ and $SiO_2$. Thus, by decomposition of the organic compounds of metals by heating, there can be formed a catalyst layer comprising at least one kind of the catalyst metals of Pt, Pd and Rh and at least one kind of carriers of $Al_2O_3$, $ZrO_2$ and $SiO_2$.

In the CO gas sensor according to this invention using a catalyst layer formed by pyrolysis of organic compounds of metals, the response characteristic to the gas to be measured is very excellent. This may be considered to be due to realization of good porous state in the catalyst layer formed by such a method. That is, a catalyst layer is required to be under porous state to the extent such that it does not prevent the gas sensitive member from contact with the gas to be measured, and, according to this method of pyrolysis of organic compounds, the organics are considered to be removed from the state in which metals are previously disposed, to form voids thereat.

Also, according to this pyrolysis of organic compounds, it is possible to obtain a catalyst layer with any desired composition easily by controlling the amounts of organic compounds of metals in an organic solvent. Further, organic compound of metals can be homogeneously dispersed in an organic solvent, whereby homogeneous compositions can be realized with good reproducibility in the catalyst layer formed and therefore reliability in case of bulk production of gas sensitive elements is excellent. Further, regardless of the shape of the substrate, homogeneous films can be formed in any of plates, cylinders, etc. Table 1 shows sensitivities to various gases of the CO gas sensor as described above.

TABLE 1

| Catalyst metal (wt.%) | | | Sensitivity (Ra/Rg) (Element temperature: 100° C.) | | | | |
|---|---|---|---|---|---|---|---|
| Pd | Pt | Rh | CO | $H_2$ | $C_3H_8$ | $CH_4$ | $C_2H_5OH$ |
| 10 | — | — | 200 | 1.2 | 1.0 | 1.0 | 100 |
| — | 10 | — | 300 | 5.0 | 1.0 | 1.0 | 150 |
| — | — | 10 | 250 | 3.0 | 1.0 | 1.0 | 180 |
| 10 | 10 | — | 500 | 6.0 | 1.0 | 1.0 | 250 |
| 10 | — | 10 | 450 | 6.5 | 1.0 | 1.0 | 200 |
| — | 10 | 10 | 600 | 2.0 | 1.0 | 1.0 | 300 |
| 10 | 10 | 10 | 650 | 7.0 | 1.0 | 1.0 | 400 |

In which:
Sensitivity (Ra/Rg):
 Ra=resistance value in air
 Rg=resistance value in the gas atmosphere to be measured
$C_2H_5OH$:
 1000 ppm
Other gases:
 200 ppm Next, a reference sensor is to be prepared as follows:
Its structure is the same as the CO gas sensor shown in FIG. 1, except that the catalyst layer was changed. The catalyst layer employed was of $Ag-Al_2O_3$ system, and it was formed in the same manner as described above by use of a dilution of an alkoxide of aluminum and a Ag resin salt (e.g. Silver resinate produced by ESL Co.) with butanol.

The gas sensitive characteristics of this reference sensor are shown in Table 2.

TABLE 2

| Sensitivity (Ra/Rg) (Element temperature: 100° C.) | | | | |
|---|---|---|---|---|
| CO | $H_2$ | $C_3H_8$ | $CH_4$ | $C_2H_5OH$ |
| 2 | 4 | 1 | 1 | 200 |

In which;
Sensitivity (Ra/Rg):
 Ra=resistance value in air
 Rg=resistance value in the gas atmosphere to be measured
$C_2H_5OH$:

1000 ppm
Other gases:
200 ppm

EXAMPLE 2

The gas sensitive member and the catalyst layer with the same constitution as in the gas sensitive element shown in FIG. 1 were formed according to the sputtering method. The characteristics of the gas sensitive element obtained had the characteristics as shown in Table 3.

CO gas sensor:
  Gas sensitive member:
    Target: $Nb_2O_5/SnO_2=0.005$ (molar ratio)
    Film thickness 1000 Å
  Catalyst layer:
    Target: $Al_2O_3$ and 50 wt.% of Pd based on $Al_2O_3$
    Film thickness: 100 Å
Reference sensor:
  Gas sensitive member: (the same as in the CO gas sensor)
  Catalyst layer:
    Target: $Al_2O_3$ and 20 wt.% of Ag based on $Al_2O_3$
    Film thickness: 100 Å

TABLE 3

|  | Sensitivity (Ra/Rg) | | |
|---|---|---|---|
|  | CO 200 ppm | $H_2$ 3000 ppm | $C_2H_5OH$ 1000 ppm |
| CO gas sensor | 22 | 15 | 20 |
| Reference sensor | 3 or less | 15 | 21 |

In which;
  Ra: Resistance value in air
  Rg: Resistance value in the gas atmosphere to be measured In the case where the catalyst layer is formed according to the sputtering method, there may be employed as the target a material containing the catalyst metals and the carrier at a desired ratio, or alternatively there may be employed as the target a material containing the catalyst metals or at least one kind of Al, Si and Zr, and after thin film formation, the thin film may be oxidized by heating under an oxygen containing atmosphere to form the catalyst layer. It is also possible to use as the target a material containing the catalyst metals and at least one kind of Al, Si and Zr and effect sputtering under an atmosphere in the presence of oxygen. In this case, for the purpose of increasing stability of the oxides to be used as the carrier, it is preferred to carry out a heating treatment in the air after formation of a thin film. The same is the case where a material containing the catalyst metals and the carrier was employed. Thus, the target to be used for the sputtering method may be either a mixture of starting material powders or an alloy thereof. Alternatively, a part of the surface of a single target material may be coated with another material to be used as the target. Further, the binary sputtering method may also be applicable, and in this case various compositions can be realized with the same targets.

Also, the catalyst layer is required to be porous to the extent such that it may not prevent the gas sensitive member from contact with the gas to be measured. When the catalyst layer is sufficiently thin, for example, with a thickness of 10 nm or less, the thin film will grow in shapes of islands even by use of the conventional sputtering method, whereby substantially porous state can be realized. It is also possible to carry out sputtering under a high gas pressure of about $10^3$ Torr, for example, Ar, $O_2N$, etc., whereby the gas is confined in the catalyst layer formed and said gas can be removed by heating to realize a porous state. Further, sputtering may be effected on a target incorporating an organic material such as PVA to form a catalyst layer containing an organic material, which organic material is then removed by heating to realize a porous state.

The gas sensor is generaly provided with a heater for heating of the gas sensitive member. Since the catalyst layer is formed in a thin film to have a reduced heat content, whereby the output of the heater can be suppressed to elongate the life of the heater, which also leads to elongation of the life of the gas sensor.

EXAMPLE 3

Now, the present invention is further illustrated by referring to an example in which the same gas sensitive member as in Example 1 was used and the catalyst layer was made as thick film by coating and sintering.

Formation of catalyst layer for CO gas sensor

An aqueous solution containing 1.0 wt.% of Pd was prepared by dissolving $(NH_4)_2PdCl_6$ in water. Into the solution were dipped fine powder of $Al_2O_3$ with a surface area of about 100 $m^2/g$, followed by thorough stirring. The $Al_2O_3$ powders were separated by filtration, dried under reduced pressure for 1.5 hours to remove water, followed by evaporation to dryness. Then, the dried mass was crushed in a mortar, and the resultant powders were placed in a quartz crucible and baked at 400° C.

The catalyst powder was added into an aqueous aluminum hydroxychloride solution (1% $Al_2O_3$) to prepare a pasty material. The pasty material was coated on the gas sensitive member, dried and the whole product was baked at 400° C. to form a catalyst layer of Pd carried on $Al_2O_3$ with a thickness of 20 um.

Formation of the catalyst layer of reference sensor $Al_2O_3$ was dipped in a predetermined amount of $AgNO_3$ solution to be impregnated with 10 wt.% of Ag and dried, followed by baking at 400° C. in a quartz crucible. The catalyst powders were added into an aqueous aluminum hydroxychloride solution (1% $Al_2O_3$) to prepare a pasty material. The pasty material was coated on the gas sensitive member, dried and the whole product was baked at 400° C. to form a catalyst layer of Ag carried on $Al_2O_3$ with a thickness of 20 $\mu m$.

In the same manner as described above, various gas sensors having the thick film catalyst layers were prepared by varying the catalyst metal species, and their gas sensitive characteristics were measured to obtain the results as shown in Table 4.

TABLE 4

| Kind of Catalyst layer | Sensitivity (Ra/Rg) 100° C. | | | | |
|---|---|---|---|---|---|
|  | CO 200 ppm | $H_2$ 200 ppm | $C_3H_3$ 200 ppm | $CH_4$ 200 ppm | $C_2H_5OH$ 1000 ppm |
| CO gas sensor: |  |  |  |  |  |
| Pd—$Al_2O_3$ | 120 | 1.0 | 1.0 | 1.0 | 24 |
| Pt—$Al_2O_3$ | 400 | 1.3 | 1.0 | 1.0 | 80 |
| Rh—$Al_2O_3$ | 220 | 1.3 | 1.0 | 1.0 | 125 |
| Pd—Pt—$Al_2O_3$ | 600 | 7.5 | 1.0 | 1.0 | 250 |
| Pd—Rh—$Al_2O_3$ | 500 | 2.0 | 1.0 | 1.0 | 340 |

TABLE 4-continued

| Kind of Catalyst layer | Sensitivity (Ra/Rg) 100° C. | | | | |
|---|---|---|---|---|---|
| | CO 200 ppm | $H_2$ 200 ppm | $C_3H_3$ 200 ppm | $CH_4$ 200 ppm | $C_2H_5OH$ 1000 ppm |
| Pt—Rh—$Al_2O_3$ Reference sensor: | 700 | 2.0 | 1.0 | 1.0 | 500 |
| Ag-$Al_2O_3$ | 1.1 | 1.3 | 1.5 | 1.03 | 270 |

In which;
Ra: resistance value in air
Rg: resistance value in the gas atmosphere to be measured

EXAMPLE 4

Prepared was the following CO gas sensor in place of those described in Example 1.

(1) Formation of $SnO_2$ thin film

Tin 2-ethylhexanoate was dissolved in n-butanol to a Sn content of 10 wt.% to prepare a sample solution. The solution was coated on the external surface of an insulating substrate 1 having previously provided a pair of electrodes as shown in FIG. 3, left to stand in the air for one hour and then heated to vaporize n-butanol. Then, the whole product was baked at 400° C. for one hour. This coating-baking step was repeated three times to form a $SnO_2$ film with a thickness of about 0.3 μm.

(2) Formation of catalyst layer

An aqueous solution containing 1.0 wt.% Pd was prepared by dissolving $(NH_4)_2PdCl_6$ in water. In this solution were dipped fine powder of $Al_2O_3$ of a surface area of 100 m²/g and the mixture was thoroughly stirred. The $Al_2O_3$ powders were separated by filtration and dried under reduced pressure at about 100° C. for 1.5 hours (1 to 2 hours in general) to remove water, followed by evaporation to dryness. The resultant solid was crushed in a mortar, and the powder obtained were baked at 400° C. (400° to 800° C. in general) in a quartz crucible.

The powder of this catalyst was thrown into an aqueous aluminum hydroxychloride solution (1% $Al_2O_3$) to prepare a pasty material. The pasty material was coated on the $SnO_2$ thin film and drying, followed by baking of the whole created product at 400° C. (300° to 400° C. in general). There was formed a catalyst of Pd-carrying $Al_2O_3$ with a thickness of 20 μm.

(3) Measurement of sensitivity characteristics

Using the CO gas sensor of this invention thus prepared, sensitivities of the element at various actuation temperature to gases of CO, $H_2$, $CH_4$, $C_3H_8$ each at a concentration of 2000 ppm and $C_2H_5OH$ at a concentration of 1000 ppm were measured as Ra/Rg. Here, Ra is a resistance value exhibited by the element in the air containing no gas to be measured and Rg is that in the air containing the gas to be measured at respective concentrations. As Ra/Rg value is greater, it means higher sensitivity. The results are summarized in FIG. 4.

Figure 5:
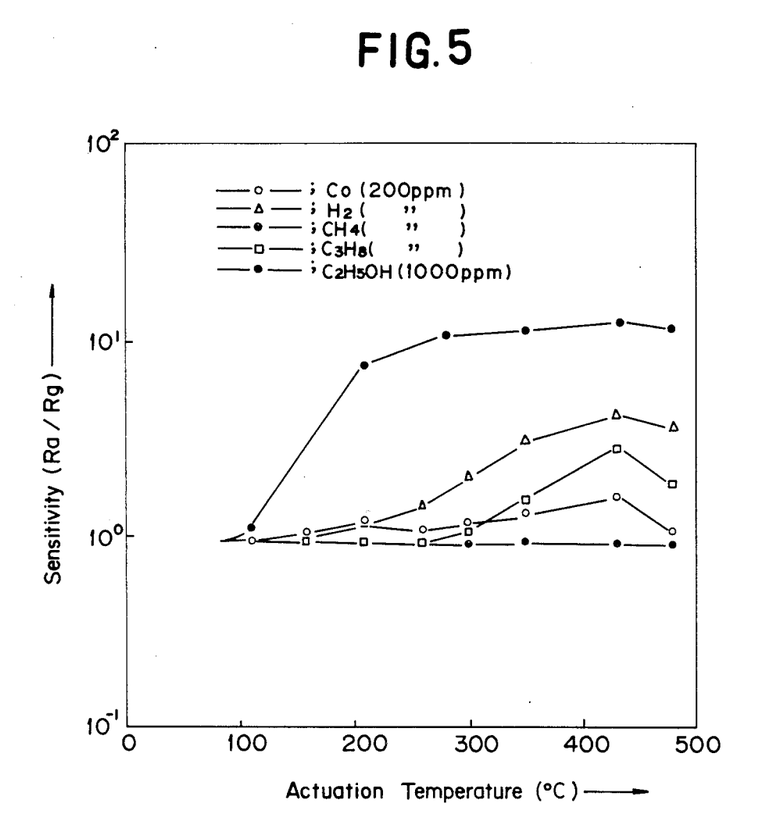
FIG. 5 is a diagram showing sensitivity characteristics of a $SnO_2$ thin film used in a gas sensitive element of the device according to this invention.

For comparison, sensitivities of the gas sensitive element provided only with the $SnO_2$ thin film layer without provision of the Pd-$Al_2O_3$ catalyst layer are shown in FIG. 5.

Figure 4:
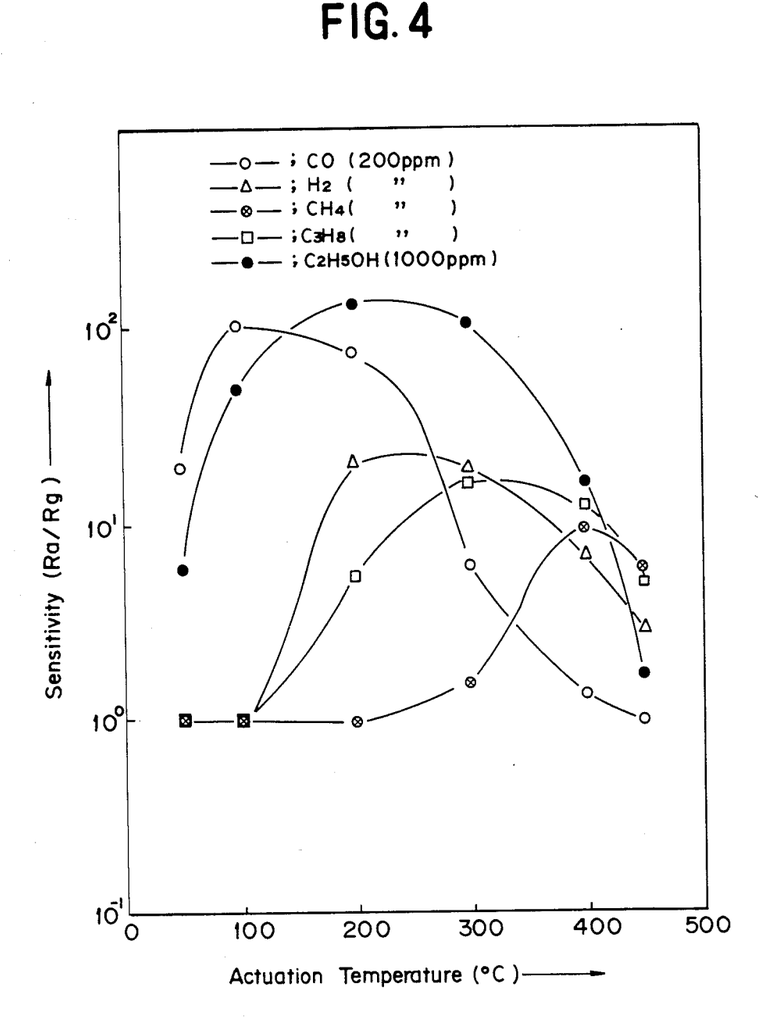
FIG. 4 is a diagram showing sensitivity characteristics to various gases of a gas sensitive element used in this invention where a the Pd(1.0 wt.%)-$Al_2O_3$ catalyst is used.

In these Figures, CO, $H_2$, $CH_4$, $C_3H_8$ and $C_2H_5OH$ are respectively represented by the symbols as shown therein.

As apparently seen from FIG. 5, the element having provided only the $SnO_2$ thin film has small sensitivities as a whole and the sensitivities to $C_2H_5OH$ are greater at all actuation temperatures. In contrast, the element of the present invention having further provided the Pd-$Al_2O_3$ catalyst layer thereon, is increased in sensitiviy as a whole as can be clearly seen from FIG. 4, and the actuation temperature beginning to exhibit sensitivities are inclined to be shifted toward the lower temperature side with variations of the sensitivity characteristics for respective gases, thus exhibiting gas selectivity depending on the actuation temperature.

In FIG. 4, referring, for example, to $C_2H_5OH$, the sensitivity to its gas concentration of 1000 ppm is at its maximum at about 300° C., but it is lowered to a value less than the sensitivity to CO of 200 ppm at about 120° C. or lower. And, at a temperature over 300° C., the sensitivity is gradually lowered, until it reaches a value lower than those to $H_2$, $CH_4$, $C_3H_8$ of 200 ppm at 420° C. or higher.

Accordingly, since the alarm concentration of $CH_4$, $C_3H_8$ is 2000 ppm or higher, when 1000 ppm of $C_2H_5$ is present, it is possible to set an alarm level for $CH_4$ or $C_3H_8$ without erroneous actuation at an actuation temperature of about 350° C. or higher. Further, when the actuation temperature is made 120° C. or lower, it is possible to set an alarm level of 200 ppm for CO without actuation error by 1000 ppm of $C_2H_5OH$.

EXAMPLE 5

According to the same procedure as in Example 4, various kinds of $SnO_2$ thin films as shown in Table 5 were formed, and further various kinds of thick film catalyst layers were provided thereon to prepare the CO gas sensor used in this invention. These sensors were subjected to measurements of sensitivities (Ra/Rg) at various actuation temperatures. The sensitivities of the respective elements at the actuation temperatures of 100° C., 350° C. and 400° C. are summarized in the Table, see Examples 5-1 to 5-17.

In the $SnO_2$ thin films, each content of Nb, Sb corresponds to 0.01 in terms of the atomic ratio to Sn. In the catalysts, those having carried each of Pd, Pt and Rh thereon all had a quantity carried of 1.0 wt.% based on the weight of $Al_2O_3$, while the quantity of Pd in case of Pd-Pt or Pd-Rh is 1.0 wt.% based on $Al_2O_3$ and Pt or Rh was 0.5 in terms of the atomic ratio to Pd. As for Pt-Rh, Pt was 1.0 wt.% based on $Al_2O_3$ and Rh was 0.5 in terms of the atomic ratio to Pt.

TABLE 5

| Example No. | Kind of $SnO_2$ thin film | Kind of catalyst layer | Sensitivity (Ra/Rg) | | | | |
|---|---|---|---|---|---|---|---|
| | | | CO 200 ppm | $H_2$ 200 ppm | $C_3H_8$ 200 ppm | $CH_4$ 200 ppm | $C_2H_5OH$ 1000 ppm |
| | | | 100° C. | | | | |
| 5-1 | $SnO_2$ | Pt—$Al_2O_3$ | 320 | 1.1 | 1.0 | 1.0 | 65 |
| 5-2 | | Rh—$Al_2O_3$ | 180 | 1.1 | 1.0 | 1.0 | 100 |
| 5-3 | | Pd—Pt—$Al_2O_3$ | 480 | 6.0 | 1.0 | 1.0 | 200 |

TABLE 5-continued

| Example No. | Kind of SnO₂ thin film | Kind of catalyst layer | Sensitivity (Ra/Rg) | | | | |
|---|---|---|---|---|---|---|---|
| | | | CO 200 ppm | H₂ 200 ppm | C₃H₈ 200 ppm | CH₄ 200 ppm | C₂H₅OH 1000 ppm |
| 5-4 | | Pd—Rh—Al₂O₃ | 400 | 1.6 | 1.0 | 1.0 | 270 |
| 5-5 | | Pt—Rh—Al₂O₃ | 550 | 1.6 | 1.0 | 1.0 | 400 |
| 5-6 | SnO₂—Nb | Pd—Al₂O₃ | 120 | 1.0 | 1.0 | 1.0 | 24 |
| 5-7 | | Pt—Al₂O₃ | 400 | 1.3 | 1.0 | 1.0 | 80 |
| 5-8 | | Rh—Al₂O₃ | 220 | 1.3 | 1.0 | 1.0 | 125 |
| 5-9 | | Pd—Pt—Al₂O₃ | 600 | 7.5 | 1.0 | 1.0 | 250 |
| 5-10 | | Pd—Rh—Al₂O₃ | 500 | 2.0 | 1.0 | 1.0 | 340 |
| 5-11 | | Pt—Rh—Al₂O₃ | 700 | 2.0 | 1.0 | 1.0 | 500 |
| 5-12 | SnO₂—Sb | Pd—Al₂O₃ | 70 | 1.2 | 1.0 | 1.0 | 29 |
| 5-13 | | Pt—Al₂O₃ | 470 | 1.5 | 1.0 | 1.0 | 95 |
| 5-14 | | Rh—Al₂O₃ | 260 | 1.6 | 1.0 | 1.0 | 150 |
| 5-15 | | Pd—Pt—Al₂O₃ | 720 | 9.0 | 1.0 | 1.0 | 300 |
| 5-16 | | Pd—Rh—Al₂O₃ | 600 | 2.5 | 1.0 | 1.0 | 400 |
| 5-17 | | Pt—Rh—Al₂O₃ | 850 | 2.5 | 1.0 | 1.0 | 600 |
| 350° C. | | | | | | | |
| 5-1 | SnO₂ | Pt—Al₂O₃ | 1.0 | 105 | 25 | 3.0 | 330 |
| 5-2 | | Rh—Al₂O₃ | 1.0 | 70 | 40 | 3.0 | 280 |
| 5-3 | | Pd—Pt—Al₂O₃ | 2.0 | 28 | 25 | 8.5 | 50 |
| 5-4 | | Pd—Rh—Al₂O₃ | 1.0 | 35 | 40 | 7.0 | 50 |
| 5-5 | | Pt—Rh—Al₂O₃ | 1.0 | 20 | 45 | 8.0 | 65 |
| 5-6 | SnO₂—Nb | Pd—Al₂O₃ | 3.6 | 16.0 | 25 | 6.8 | 50 |
| 5-7 | | Pt—Al₂O₃ | 1.1 | 13.5 | 30 | 4.0 | 400 |
| 5-8 | | Rh—Al₂O₃ | 1.0 | 90 | 54 | 4.0 | 350 |
| 5-9 | | Pd—Pt—Al₂O₃ | 2.6 | 35 | 30 | 10.5 | 65 |
| 5-10 | | Pd—Rh—Al₂O₃ | 1.2 | 42 | 50 | 9.2 | 60 |
| 5-11 | | Pt—Rh—Al₂O₃ | 1.1 | 25 | 60 | 10 | 80 |
| 5-12 | SnO₂—Sb | Pd—Al₂O₃ | 4.3 | 19 | 30 | 8.2 | 60 |
| 5-13 | | Pt—Al₂O₃ | 1.3 | 16 | 35 | 4.8 | 470 |
| 5-14 | | Rh—Al₂O₃ | 1.2 | 100 | 65 | 4.7 | 420 |
| 5-15 | | Pd—Pt—Al₂O₃ | 3.1 | 40 | 34 | 12.8 | 80 |
| 5-16 | | Pd—Rh—Al₂O₃ | 1.4 | 50 | 60 | 11.0 | 70 |
| 5-17 | | Pt—Rh—Al₂O₃ | 1.2 | 30 | 70 | 12.5 | 95 |
| 400° C. | | | | | | | |
| 5-1 | SnO₂ | Pt—Al₂O₃ | 1.0 | 9.6 | 20 | 4.9 | 17 |
| 5-2 | | Rh—Al₂O₃ | 1.0 | 1.5 | 32 | 4.5 | 25 |
| 5-3 | | Pd—Pt—Al₂O₃ | 1.0 | 14 | 14 | 12 | 17 |
| 5-4 | | Pd—Rh—Al₂O₃ | 1.0 | 10 | 17 | 11.5 | 14 |
| 5-5 | | Pt—Rh—Al₂O₃ | 1.0 | 8 | 20 | 14 | 16 |
| 5-6 | SnO₂—Nb | Pd—Al₂O₃ | 1.7 | 8.6 | 16.5 | 12.5 | 21 |
| 5-7 | | Pt—Al₂O₃ | 1.0 | 12 | 25 | 6.4 | 20 |
| 5-8 | | Rh—Al₂O₃ | 1.0 | 1.9 | 40 | 6.0 | 30 |
| 5-9 | | Pd—Pt—Al₂O₃ | 1.2 | 18 | 18 | 15 | 21 |
| 5-10 | | Pd—Rh—Al₂O₃ | 1.0 | 12.5 | 21.5 | 15 | 18 |
| 5-11 | | Pt—Rh—Al₂O₃ | 1.0 | 10 | 25 | 17 | 20 |
| 5-12 | SnO₂—Sb | Pd—Al₂O₃ | 2.0 | 10.4 | 20 | 15.0 | 25 |
| 5-13 | | Pt—Al₂O₃ | 1.2 | 14.5 | 30 | 7.7 | 24 |
| 5-14 | | Rh—Al₂O₃ | 1.2 | 2.3 | 48 | 7.0 | 36 |
| 5-15 | | Pd—Pt—Al₂O₃ | 1.5 | 22 | 21 | 18 | 23 |
| 5-16 | | Pd—Rh—Al₂O₃ | 1.2 | 15 | 25 | 17 | 22 |
| 5-17 | | Pt—Rh—Al₂O₃ | 1.2 | 12 | 30 | 20 | 25 |

As is apparently seen from Table 5, the CO gas sensor used in this invention exhibits a particularly high sensitivity to CO, exhibiting a 100-fold or higher value to the concentration of 200 ppm. It is also highly sensitive by 10- to 70-fold to CH₄ and C₃H₈. Also, the sensitivity to C₂H₅OH is lowered gradually as the temperature is higher than 300° C., and at 420° C., the sensitivity value to 1000 ppm of C₂H₅OH is lower than those to 200 ppm of CH₄ or C₃H₈.

In the following Examples 6 and 7, described are examples where the catalyst layer of the CO gas sensor used in this invention further contains Ag or is covered with another catalyst layer containing Ag.

EXAMPLE 6

Prescribed amount of tin octylate was weighed and dissolved in n-butanol to a content of 10 wt.% to prepare a solution of tin octylate, which was then coated on an insulating substrate having a pair of electrodes 2, 2' in the same manner as shown in FIG. 3, left for 30 minutes to dryness in the air, and further left for 30 minutes to dryness at 120° C. in the air to make n-butanol evaporated. The product thus obtained was successively baked at 400° to 700° C. for 30 minutes to obtain a plate-like gas sensitive member 5 comprising a SnO₂ thin film with a thickness of 0.5 μm. In this case it is generally preferable to carry out rapid heating and cooling, and also to repeat once to four times the steps of coating and baking in order to control the film thickness.

Thereafter, a catalytic substance obtained by thoroughly mixing a solution of paradium chloride added with prescribed amount of Al₂O₃ powder and a catalytic substance obtained by thoroughly mixing a solution of silver nitrate added with prescribed amount of Al₂O₃ powder were mixed. The mixture was then left for 1 to 2 hours to dryness under reduced pressure, and further dried thoroughly at 100° C., and the dried product thus obtained was ground into powder and baked at 400° to 800° C. in a quartz crucible to prepare a catalyst containing 1 wt.% of Pd and 1 wt.% of Ag based on Al₂O₃. This catalyst was then coated on the surface of the above-mentioned gas sensitive member 5, followed by baking at about 300° to 400° C. to form a catalyst layer 6. A CO gas sensor to be used in the invention was thus obtained.

Besides the above sensor having the catalyst layer containing Pd and Ag, also prepared were those empolying Pt and/or Rh, and a mixture of Pd and Pt or Rh.

Sensitivity characteristics of these sensors at actuation temperature of about 350° C. were measured in the same manner as in Example 4. Results are shown in Table 6, see Example Nos. 6-1 to 6-6.

EXAMPLE 7

Following the procedures of Example 6, prepared was a plate-like gas sensitive member 5.

Next, after thorough mixing of a solution of palladium chloride added with prescribed amount of $Al_2O_3$ powder, the mixture was left for 1 to 2 hours to dryness under reduced pressure, and further dried thoroughly at 100° C. The dried product was then ground into powder and baked at 400° to 800° C. by using a quartz crucible to prepare a catalyst containing 1 wt.% of Pd. The catalyst thus obtained was coated on the outer surface of the above-mentioned gas sensitive member, which was then baked at about 300° to 400° C. to form a catalyst layer 6 as a first catalyst layer with a thickness of 20 μm.

Subsequently, after thorough mixing of a solution of silver nitrate added with prescribed amount of $Al_2O_3$ powder, and a catalyst containing 10 wt.% of Ag was prepared in the same manner as in the preparation of the above-mentioned catalyst. Thereafter, the catalyst was coated on the first catalyst layer 6, followed by baking at about 300° to 400° C. to form thereon a second catalyst layer (not shown) with a thickness of 30 μm. A CO gas sensor having the above first and second catalyst layers was thus obtained.

Besides the above sensor having the first catalyst layer containing Pd, also prepared were those employing the first catalyst layers containing Pt and/or Rh, and a mixture of Pd and Pt or Rh, on which the second catalyst layers containing Ag were provided.

Sensitivity characteristics of these sensors at actuation temperature of about 350° C. were measured in the same manner as in Example 4. Results are shown in Table 6, see Example Nos. 7-1 to 7-6.

Figure 6:
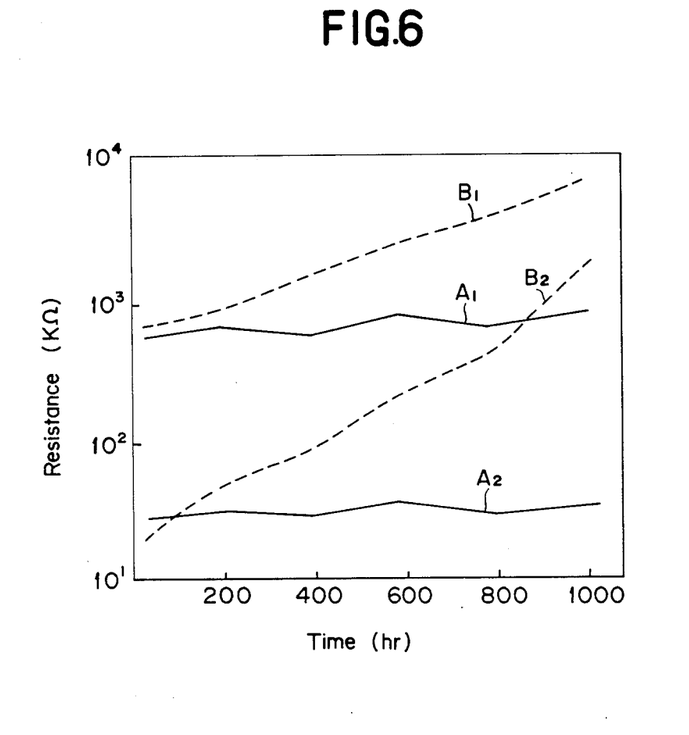
FIG. 6 is a diagram showing a time lapse change of resistance observed by CO gas electroconductive test on a gas sensitive element of the device according to this invention and a comparative example at 30° C., 90% RH in air and 30° C., 90% RH in CO gas, respectively.

Changes, as time lapses, in resistance value in the air (Ra) at 30° C. under 90% RH and resistance value in CO gas (Rg) at 30° C. under 90% RH of the respective CO gas sensors of the Example and the comparative example were examined. Results are shown in FIG. 6, in which $A_1$ and $A_2$ denote a characteristic curve showing changes in the resistance value in the air under high humidity and a characteristic curve showing changes in the resistance value in CO gas under high humidity, respectively, of the CO gas sensor according to this invention; $B_1$ and $B_2$ denote a characteristic curve showing changes in the resistance value in the air under high humidity and a characteristic curve showing changes in the resistance value in CO gas under high humidity, respectively, of the CO gas sensor according to the comparative example.

As is apparent from FIG. 6, the CO gas sensor according to the comparative example provided with the catalyst layer containing Pd only shows both Ra and Rg gradually hightened and sensitivity (Ra/Rg) lowered. Contrary thereto, the CO gas sensor according to this invention provided with the catalyst layer containing Pd and Ag shows extreme stability without any affection by humidity, and was found to have humidity resistance.

Although there were employed CO gas sensors having gas sensitive member comprising $SnO_2$ in the above Example, substantially the same results were obtained from the members made of other metal oxides such as $ZnO_2$, $Fe_2O_3$, etc.

Moreover, although there was employed $Al_2O_3$ as insulating material for the catalyst, substantially the same results were obtained also when $SiO_2$, $ZrO_2$ or a mixture of any of $Al_2O_3$, $SiO_2$ and $ZrO_2$.

As can be seen from the above descriptions, the CO gas sensor according to this invention has sensitivities to CO gas and miscellaneous gases such as of alcohols, while the reference sensor has no substantial sensitivity to CO gas but has sensitivities to miscellaneous gases such as of alcohols. Accordingly, by use of the output of the reference sensor, the influence of the miscellaneous gases such as of alcohols can be readily removed to enable detection of CO gas with good selectivity. In addition, the CO gas sensor has very low sensitivities to the gases such as $H_2$, $CH_4$, $C_3H_8$, etc., thus exhibiting still improved selectivity.

TABLE 6

| Example No. | First catalyst layer | Second catalyst layer | Sensitivity (Ra/Rg) 350° C. | | | | |
|---|---|---|---|---|---|---|---|
| | | | CO 200 ppm | $H_2$ 200 ppm | $C_3H_8$ 200 ppm | $CH_4$ 200 ppm | $C_2H_5OH$ 1000 ppm |
| 6-1 | Pd—Ag—$Al_2O_3$ | — | 2.5 | 12 | 15 | 4.1 | 75 |
| 6-2 | Pt—Ag—$Al_2O_3$ | — | 1.5 | 95 | 23 | 2.8 | 350 |
| 6-3 | Rh—Ag—$Al_2O_3$ | — | 1.5 | 64 | 36 | 2.6 | 300 |
| 6-4 | Pd—Pt—Ag—$Al_2O_3$ | — | 2.4 | 25 | 26 | 7.7 | 63 |
| 6-5 | Pd—Rh—Ag—$Al_2O_3$ | — | 1.3 | 32 | 34 | 6.3 | 64 |
| 6-6 | Pt—Rh—Ag—$Al_2O_3$ | — | 1.2 | 18 | 41 | 7.2 | 78 |
| 7-1 | Pd—$Al_2O_3$ | Ag—$Al_2O_3$ | 2.3 | 10 | 13 | 6.9 | 67 |
| 7-2 | Pt—$Al_2O_3$ | " | 1.2 | 87 | 20 | 2.5 | 310 |
| 7-3 | Rh—$Al_2O_3$ | " | 1.2 | 57 | 32 | 2.3 | 272 |
| 7-4 | Pd—Pt—$Al_2O_3$ | " | 2.1 | 23 | 24 | 7.2 | 61 |
| 7-5 | Pd—Rh—$Al_2O_3$ | " | 1.2 | 30 | 33 | 6.0 | 60 |
| 7-6 | Pt—Rh—$Al_2O_3$ | " | 1.1 | 16 | 39 | 6.8 | 75 |

As a comparative example, on the other hand, further prepared was a CO gas sensor in the same manner as in the Example except that provided on the outer surface of the gas sensitive member was a catalyst layer containing 1.0 wt.% of Pd and not containing Ag.

Figure 7:
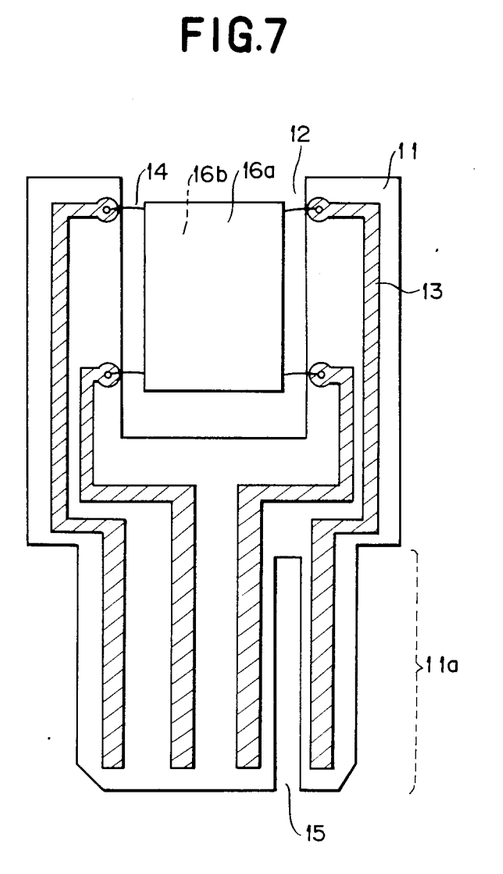
FIG. 7 is a plan view of an example of the device according to this invention.

In the following, descriptions are given with respect to an example of construction of the CO gas detecting device of this invention and an example of application thereof to a circuit:

The CO gas sensor and the reference sensor formed as described above may be fixed respectively on separate supporting plates, but they may be fixed on one supporting plate in view of miniaturization of the device, etc. FIG. 7 shows a plan view of an embodiment in which the CO gas sensor and the reference sensor are fixed on one supporting plate.

On an insulating supporting plate 11 comprising a glass epoxy resin and having a plug portion 11a, there is provided a cut area 12 for suspending therein the gas sensitive elements. The insulating supporting plate 11 has conductor patterns 13 comprising Cu foil formed on both of front and rear surfaces thereof, and the CO gas sensor 16a and the reference sensor 16b are secured and suspended within the cut area 12 by lead wires 14, made of Pt, of about 100 μm diameter in the manner that they are respectively located on the faces corresponding to the front surface and the rear surface of the supporting plate 11. Also, since the gas sensitive elements with different characteristics are provided on both surfaces of the supporting plate 11, another cut 15 is provided at an area adjacent to and along one side of the plug portion 11a in such a manner that it may be inserted to the corresponding plug socket having a shape corresponding to the sectional shape of the plug thus formed. This is for the purpose of avoiding errors in the direction when, for example, inserting the device into an external plug socket. Further, for improvement of abrasion resistance, it is preferred to apply Ni plating on the surface of the conductor pattern 13.

Although there is shown in the above an example where the CO gas sensor 16a and the reference sensor 16b are provided on the respective faces of the supporting plate 11, they may alternatively be provided in parallel on the same face corresponding to one surface of the supporting plate 11.

Moreover, there was employed in this embodiment a glass epoxy resin on which Cu foil was formed, but it is also possible to use an $Al_2O_3$ supporting plate on which Au is baked.

By taking such a structure having two gas sensitive elements suspended in the cut area 12 of the supporting plate 11, good ventilation can be ensured for the atmosphere to be measured. Further, heating efficiency of the gas sensitive member by the heater in the heat sensitive member, which is usually actuated at higher temperatures (e.g. 100° C. or higher), can also be improved, because thermal conduction to the supporting plate 11 occurs substantially only through the lead wires.

Figure 8:
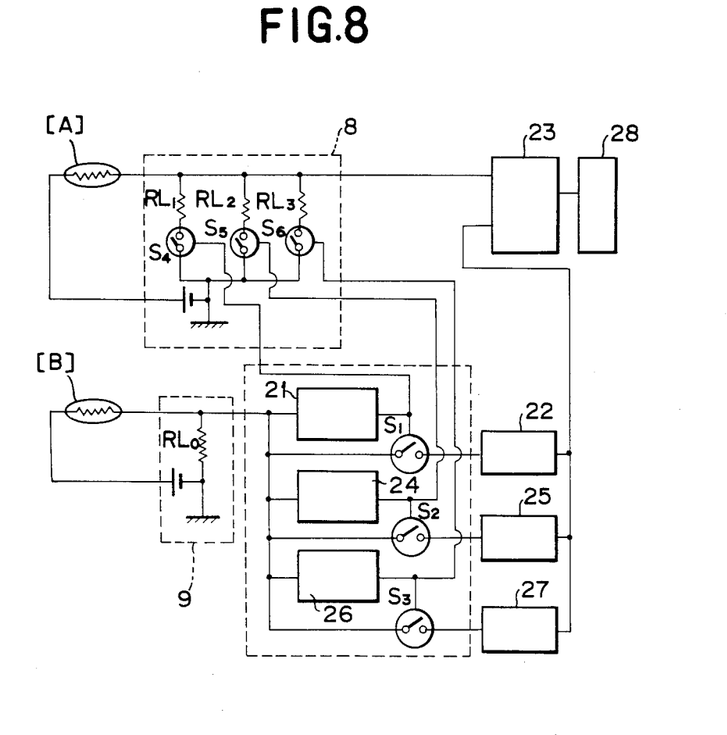
FIG. 8 is a block diagram showing a more specific example of a circuit for driving the device of this invention.

Referring next to the block diagram in FIG. 8, a more specific example of the circuit constitution for actuating the CO gas detecting device of the present invention is described below:

In FIG. 8, $S_1$ through $S_6$ are switches electrically operable. First, when there is no miscellaneous gas in the air and the reference sensor [B] has a high resistance, the voltage between both terminals of $R_{L0}$ is low. Under this state, the voltage comparison circuit 21 actuates to turn on the switches $S_1$ and $S_4$. As a result, the CO gas sensor [A] generates a voltage output with the use of a relatively large resistor $R_{L1}$, which output is compared with the signal in the alarm level setting circuit 22 by the second voltage comparison circuit 23. When CO gas is introduced with such a circuit constitution, the resistance of the detecting element is lowered but the reference sensor [B] undergoes no change in resistance, and therefore the voltage between both terminals of $R_{L1}$ and the output of the alarm level setting circuit 22 are inputted and judged in the second voltage comparison circuit 23. In this case, due to presence of only CO gas, the extent of output saturation by the detecting element is small to give sufficiently stable alarm.

Next, when miscellaneous gases are present in the air, the resistance of the reference sensor [B] is lowered, to result in increase in the voltage between both terminals of $R_{L0}$. In this case, when the voltage between both terminals of $R_{L0}$ exceeds the region of the first voltage comparison circuit 21, the first voltage comparison circuit 21 stops its actuation, thus turning off the switches $S_1$ and $S_4$, simultaneously with turning on of the switches $S_2$ and $S_5$, whereby $R_{L2}$ and the alarm level setting circuit 25 are actuated. In this case, because the resistance of the CO gas sensor is also reduced, $R_{L2}$ employed is made smaller than $R_{L1}$. When a gas to be tested is introduced under such a state, the CO gas sensor [A] is further changed in resistance to elevate the voltage between both terminals of $R_{L2}$. This is judged by comparison with the output of the alarm level setting circuit 24 by the second voltage comparison circuit 23. In this case, since the resistance value of the CO gas sensor [A] is reduced by the miscellaneous gases, the signal can be read with better precision rather by use of $R_{L2}$ than by use of $R_{L1}$ ($R_{L1} > R_{L2}$).

At higher levels of miscellaneous gas concentrations, this method can be of course utilized to capture the gas to be tested surely at high precision and emit the alarm. In FIG. 8, numerals 8 and 9 represent resistance-voltage converting circuits, 21, 24 and 26 the first voltage comparators, and 22, 25 and 27 alarm level setting circuits, respectively, and these sections actuate similarly as described above. An alarm circuit is represented by 28.

For testing, CO gas detection was performed in the presence of miscellaneous gases by means of the CO gas detecting device with such a constitution as described already.

In the same circuit as shown in FIG. 8, $S_1$ through $S_6$ were employed as analog switches, and $R_{L0}$ was made constant, while $R_{L1}$ to $R_{L3}$ 1MΩ, 100KΩ and 10KΩ, respectively, others being the same as in conventional electronic circuits.

The measurement was conducted by first introducing only CO gas at a level of 200 ppm into the air and the circuit was set so as to emit the alarm at this value, and then the CO concentrations at the time of alarm were examined in the presence of miscellaneous gases (alcohol). The results are shown in Table 7.

TABLE 7

| Alcohol concentration: | 100 | 200 | 500 | 1000 | 2000 |
|---|---|---|---|---|---|
| CO concentration: | 200 | 200 | 200 | 210 | 215 |
| | | | | | (unit: ppm) |

As is apparently seen from Table 7, in the present invention, CO gas can be detected with very good stability.

In the above embodiment as shown in FIG. 8, switching of the circuits was made at three-stages, but further increased stages may also be available for further improvement of precision. If desired, it is of course possible to use a two-stage switching.

We claim:
1. A CO gas detecting device comprising:
   a CO gas sensor provided with a gas sensitive member comprising an oxide semiconductor whose resistance value is changed when contacted with a reducing gas, a pair of electrodes provided on said gas sensitive member, and a catalyst layer comprising one or more catalyst metals selected from the group consisting of Pt, Pd and Rh and at least one carrier selected from the group consisting of $Al_2O_3$, $ZrO_2$ and $SiO_2$, provided on said gas sensitive member; and a reference sensor substantially without sensitivity to CO gas provided with a gas sensitive member comprising an oxide semiconductor whose resistance value is changed when contacted with a reducing gas, a pair of electrodes provided on said gas sensitive member, and an insulative catalyst layer comprising Ag and at least one carrier selected from the group consisting of $Al_2O_3$, $ZrO_2$ and $SiO_2$, provided on said gas sensitive member wherein said catalyst layers of each of said sensors comprise said catalyst metals in an amount of from about 0.05 to 20 wt. % based on the catalyst carrier in a thick film of from 10 to 50 μm and from about 1 to 90 wt. % based on the catalyst carrier in a thin film of from about 5 to 1000 nm, such that the amounts of said catalyst metals are below levels at which the electroconductivity of said layers hampers measurement of said resistance value.

2. The CO gas detecting device according to claim 1, wherein the oxide semiconductor used in each of said gas sensitive members comprises at least one oxide semiconductor selected from the group consisting of $SnO_2$, ZnO and $Fe_2O_3$.

3. The CO gas detecting device according to claim 2, wherein the oxide semiconductor further comprises Nb or Sb within the range of from 0.005 to 0.05 in terms of atomic ratio to the oxide semiconductor.

4. The CO gas detecting device according to claim 1, wherein each of said gas sensitive members is a thin film.

5. The CO gas detecting device according to claim 4, wherein each of said gas sensitive member has a film thickness of from 100 Å to 1 μm.

6. The CO gas detecting device according to claim 4, wherein each of said gas sensitive members comprises a $SnO_2$ thin film or a $SnO_2$ thin film comprising Nb or Sb.

7. The CO gas detecting device according to claim 1, wherein the catalyst carrier of said CO gas sensor comprises $Al_2O_3$.

8. The CO gas detecting device according to claim 1, wherein the catalyst layer of said CO gas sensor comprises a thick film.

9. The CO gas detecting device according to claim 1, wherein the catalyst metal of said CO gas sensor is a material selected from the group consisting of Pt-Pd, Pd-Rh and Pt-Rh wherein the proportion of Pt/Pd, Rh/Pd and Rh/Pt=0.05 to 1.0, respectively, in terms of atomic ratio.

10. The CO gas detecting device according to claim 1, the catalyst layer of said CO gas sensor further comprising a moisture protective metal containing 0.05 to 20 wt.% of Ag based on the carrier(s).

11. The CO gas detecting device according to claim 1, further including another layer comprising at least one carrier of $Al_2O_3$, $ZrO_2$ and $SiO_2$ and 0.05 to 20 wt.% of Ag based on the carrier(s).

12. The CO gas detecting device according to claim 1, wherein the carrier of the catalyst layer of said reference sensor is $Al_2O_3$.

13. The CO gas detecting device according to claim 1, wherein the catalyst layer of said reference sensor comprises a thick film.

14. The CO gas detecting device according to claim 1, wherein the CO gas sensor and the reference sensor are secured and suspended within a cut area provided in an insulating supporting plate comprising a glass epoxy resin or $Al_2O_3$ and having conductor patterns comprising Cu foil formed on both of front and rear surfaces thereof, by means of lead wires in such a manner that they are respectively located on the faces corresponding to the front surface and the rear surface of the supporting plate or that they are provided in parallel on the same face corresponding to one surface of the supporting plate; said supporting plate being provided with a cut at an area adjacent to and along one side of the plug portion in such a manner that it may be inserted to an external plug socket having a shape corresponding to the sectional shape of the plug.

15. A circuit for driving the CO gas detecting device of claim 1, which comprises the CO gas sensor connected to a resistance-voltage converting circuit, the reference sensor connected to another resistance-voltage converting circuit which is further connected to an alarm level-setting circuit, a voltage comparison circuit to compare signals from the CO gas sensor and signals from the alarm level-setting circuit, and an alarm circuit to which an alarm signal from the voltage comparison circuit is inputted.

16. The CO gas detecting device according to claim 1, wherein said CO sensor and said reference sensor have similar sensitivities to reducing gases other than CO.

* * * * *